US012797219B2

(12) United States Patent
Hahlbrock

(10) Patent No.: US 12,797,219 B2
(45) Date of Patent: Nov. 17, 2026

(54) METHOD FOR PRODUCING AN ORTHOPAEDIC SUPPORT ELEMENT, AND ORTHOPAEDIC SUPPORT ELEMENT

(71) Applicant: David Hahlbrock, Cologne (DE)

(72) Inventor: David Hahlbrock, Cologne (DE)

( * ) Notice: Subject to any disclaimer, the term of this patent is extended or adjusted under 35 U.S.C. 154(b) by 364 days.

(21) Appl. No.: 18/018,234

(22) PCT Filed: Jul. 27, 2021

(86) PCT No.: PCT/EP2021/071063
§ 371 (c)(1),
(2) Date: Jan. 26, 2023

(87) PCT Pub. No.: WO2022/023376
PCT Pub. Date: Feb. 3, 2022

(65) Prior Publication Data

US 2023/0255810 A1 Aug. 17, 2023

(30) Foreign Application Priority Data

Jul. 28, 2020 (DE) ..................... 10 2020 119 920.1

(51) Int. Cl.
*A61F 5/01* (2006.01)
*B29C 33/38* (2006.01)

(52) U.S. Cl.
CPC ........... *A61F 5/0111* (2013.01); *A61F 5/0118* (2013.01); *B29C 33/3857* (2013.01); *B29C 2033/3871* (2013.01)

(58) Field of Classification Search
CPC ........ A61F 5/01; A61F 5/0104; A61F 5/0106; A61F 5/0109; A61F 5/0111; A61F 5/0118; A61F 5/05; A61F 5/058; A61F 5/05841; A61F 5/0585; A61F 5/05858; A61F 5/05866; A61F 13/04; A61F 13/06;
(Continued)

(56) References Cited

U.S. PATENT DOCUMENTS 3,541,646 A 11/1970 Baudou
5,836,902 A 11/1998 Gray
(Continued)

FOREIGN PATENT DOCUMENTS

GB 2580413 A 7/2020

OTHER PUBLICATIONS

DPMA, Examination Report, Apr. 19, 2021 re German Patent Application No. 10 2020 119 920.1 with English translation.

*Primary Examiner* — Keri J Nelson
(74) *Attorney, Agent, or Firm* — Perry + Currier Inc.

(57) ABSTRACT

The present invention relates to a method for producing an orthopaedic support element (1) having an overlap portion (2) in which the orthopaedic support element overlaps itself when it is applied to a body part that is to be corrected, wherein a manufacturing configuration (25) of the orthopaedic support element (1) is predefined for the production thereof, which manufacturing configuration (25) deviates from a therapy configuration (26) of the orthopaedic support element (1) when applying the latter to the body part that is to be corrected, wherein in the manufacturing configuration (25), in the overlap portion (2), a spacing (24) exists between a first open end (22) and the second open end (23) of the orthopaedic support element (1), which spacing (24) is not present in the therapy configuration (26).

7 Claims, 4 Drawing Sheets

Figure 1:
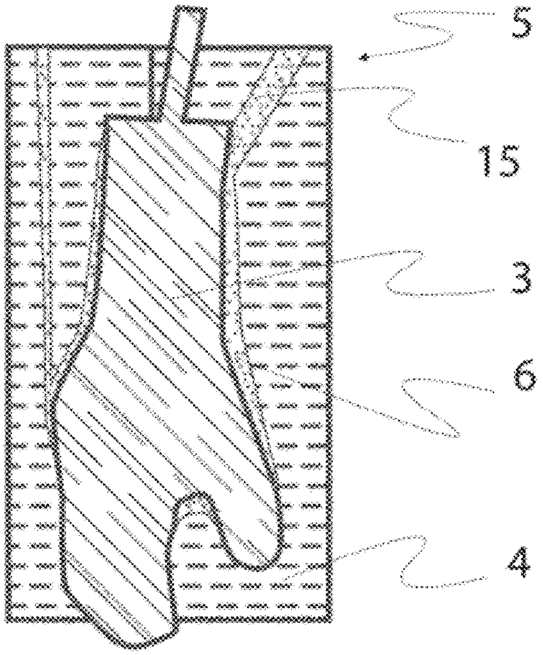

(58) Field of Classification Search
CPC .... A61F 13/061; A61F 13/062; A61F 13/064; A61F 13/066; A61F 13/10; A61F 13/101; A61F 13/102; A61F 13/104; A61F 13/107; A61F 13/108; B29C 33/3857; B29C 2033/3871; B29D 35/0018; B29D 35/02
See application file for complete search history.

(56) References Cited

U.S. PATENT DOCUMENTS

| | | | | |
|---|---|---|---|---|
| 6,186,966 | B1* | 2/2001 | Grim | D04B 1/22 128/878 |
| 8,771,212 | B1 | 7/2014 | Garris et al. | |
| 2010/0036300 | A1* | 2/2010 | Sheehan | A61F 5/05825 602/7 |
| 2011/0092867 | A1 | 4/2011 | Watts | |
| 2013/0317789 | A1* | 11/2013 | Summit | A61F 5/0123 703/1 |
| 2014/0257162 | A1* | 9/2014 | Falkenman | A43B 7/20 29/592 |
| 2016/0339607 | A1 | 11/2016 | Munoz et al. | |
| 2017/0135839 | A1* | 5/2017 | Ducharme | A61F 5/0111 |
| 2017/0216078 | A1 | 8/2017 | Rivlin et al. | |
| 2019/0336317 | A1 | 11/2019 | Madden et al. | |

* cited by examiner

METHOD FOR PRODUCING AN ORTHOPAEDIC SUPPORT ELEMENT, AND ORTHOPAEDIC SUPPORT ELEMENT

The invention relates to a method for producing an orthopedic support element and to a corresponding orthopedic support element produced by this method. Such orthopedic support elements are usually also referred to as "orthoses". Such orthopedic support elements are used to correct body part abnormalities or to support limited-mobility body parts, for example for wrists or ankles, that have an abnormality. Such orthopedic support elements can be placed against the body part with the abnormality and exert a gentle pressure on the body part. The abnormality is thus corrected and/or the body part is supported.

To produce such orthopedic support elements, the use of what is referred to as a molding as a starting point is known. The molding, preferably consisting of a plaster cast, represents the correct position or supported position of the outer shape of the body part to be corrected. The orthopedic support element is created on the basis of this molding. The use of silicone as material for such an orthopedic support element is also known.

According to a known production method for orthopedic support elements of this type, the silicone is brought to the corresponding thickness using a roller and then applied to the molding. This is frequently done by manually depositing and shaping the silicone on the plaster cast. The orthopedic support element, or the material of the orthopedic support element, is reinforced at certain points (depending on the therapeutic need). If appropriate, manual closure mechanisms and an identifier prescribed by the legislator are also fastened on and to the orthopedic support element later on.

However, this method allows only limited edge lengths of the rolled-out silicone and therefore cannot be used for large orthoses (e.g. torso). This is due to the fact, for example, that only silicone rollers with certain edge lengths are available, and that the production method can be carried out precisely only for orthopedic support elements up to a certain size. A further problem of this method is the deaeration of the material (usually silicone). Degassing the silicone, which is done manually by puncturing the gas bubbles on the roller, is particularly complex. A further frequently arising problem is sagging of the material. Since the silicone has not yet reached the end of its pot life or its vulcanization time when it is being deposited, the orthosis runs and visibly sags.

A further known production method for orthopedic support elements/orthoses of this type is the conventional molding method. In this method, the material of the orthopedic support element is introduced into a casting mold which is filled with liquid casting material. This casting material may also be silicone, for example. However, the production of a casting mold for a conventional molding process is similarly complex to the production of a silicone orthosis by the rolling method. In addition, there is a high proportion of manual work in the process of the conventional molding method. However, this method cannot be used to produce orthopedic support elements with an overlapping portion.

Taking this as a starting point, an object of the present invention is to solve, or to circumvent, or at least to alleviate the presented disadvantages of the prior art. The intention in particular is to disclose a particularly advantageous method for producing an orthopedic support element which alleviates the described disadvantages of the known method. Moreover, the intention is to specify a particularly advantageous orthopedic support element which is producible by the method and can be placed particularly easily and precisely against the body part to be treated.

Said object is achieved by a method and by an orthopedic support element according to the independent claims. Further advantageous configurations of the method are specified in the dependently formulated claims. The exemplary embodiments specified in the dependent claims and the description can be combined in any desired, technically meaningful way.

The invention relates to a method for producing an orthopedic support element having an overlapping portion, in which the orthopedic support element overlaps itself when it is placed against a body part to be corrected, wherein, for the production, a manufacturing shaping of the orthopedic support element is predefined, which manufacturing shaping differs from a therapy shaping of the orthopedic support element when being placed against the body part to be corrected, wherein there is a distance between a first open end and the second open end of the orthopedic support element in the overlapping portion of the manufacturing shaping that is not present in the therapy shaping.

It is particularly preferable when the method comprises a casting method and wherein the distance between a first open end and a second open end of the orthopedic support element in the manufacturing shaping is predefined by a mold portion of the casting mold.

The casting mold (theoretically) can be subdivided into an inner mold and outer mold. In many embodiment variants, the inner mold and the outer mold are actually different mold parts. That part of the casting mold which corresponds to the molding conventional in known methods for producing orthopedic support elements is to be assigned to the inner mold. All other portions of the casting mold are to be assigned to the outer mold. The mold portion described above, the effect of which is to produce the distance, is to be assigned to the outer mold. When an explanation is given of the inner mold and the outer mold in the following paragraphs, it always relates both to multi-part casting molds with separable inner mold and outer mold and to unipartite casting molds, in the case of which the inner mold and outer mold are connected to one another.

The invention in particular relates to a method for producing an orthopedic support element having an overlapping portion, in which the orthopedic support element overlaps itself when it is placed against a body part to be corrected, said method having the following steps:

a) providing an inner mold, which predefines a posture of the body part,
b) providing an outer mold, wherein the outer mold together with the inner mold forms a casting mold for producing the orthopedic support element from a casting material,
c) casting the orthopedic support element using the casting mold, formed from the outer mold and inner mold, and at least one casting material.

In the process, the outer mold surrounds the overlapping portion at least in certain portions on both sides.

The orthopedic support element can also be referred to as orthosis. It serves to correct an orthopedic abnormality of a body part. To correct such an abnormality, the orthopedic support element can be placed against the body part. The method is particularly suitable for the production of orthoses for supporting ankles and wrists, which orthoses can treat an ankle or wrist abnormality. Accordingly, body parts included here are, for example, ankles or wrists or else all other body parts to which orthoses can be applied, in particular arms, legs, or parts of arms or parts of legs, etc. A body part included here, however, is also the upper body, because the spinal column can also be treated by an orthosis.

The orthopedic support element can be used to correct abnormalities of a body part. For example, given an unnatural wrist or ankle position, it is possible for the orthopedic support element to exert a gentle but permanent pressure on the wrist or ankle. This gentle but continuous pressure corrects the position of the wrist or ankle very carefully.

Such an orthopedic support element, or such an orthosis, can also be applied in the foot region. This can be done, for example, in order to support walking and running Given significant deformations of the foot, a mold that makes it possible to roll the deformed foot on the ground can be produced.

The method described makes it possible to produce significantly more complex orthopedic support elements than the conventional method for producing orthopedic support elements (or orthoses) does, in particular because the design freedom of the casting mold is considerably greater than the freedom in conventional production methods, which are substantially based on bringing a lobe-shaped starting product into the desired shape of the orthopedic support element.

By virtue of the overlapping region described, the orthopedic support element can be placed against the body part in the manner of a wrap or in the manner of a sleeve. The overlapping region makes it possible in particular for the orthopedic support element to completely cover the body part in the relevant region in which the orthopedic element is intended to act, and no free region, in which the body part is not covered or spanned by the orthopedic support element, remains. In the case of orthopedic support elements without such an overlapping region, a gap at which the body part is not covered by the orthopedic support element always remains. Indeed, such a gap can have a very small to zero width. However, such a gap is often perceived as uncomfortable by the wearer of an orthopedic support element.

The inner mold provided in step a) is usually also referred to as molding. In the method described, it forms a core inserted into the casting mold. The inner mold provided already represents a corrected position into which the body part to be corrected is to be brought by the orthopedic support element. This inner mold can, for example, be produced by an impression of the body part to be corrected, wherein the shape of this impression is subsequently adapted for the purposes of the treatment to be applied to the body part. When the body part, for example, has a undesirable misalignment, the impression for the production of the inner mold is corrected such that this misalignment is counteracted. Comprehensive methods used by orthopedic technicians exist for the production of the inner mold from an imprint. The selection of a suitable method, however, is not important for carrying out the method according to the invention described here. The method described here can be applied to inner molds that were produced in any desired way.

The inner mold, or the molding, is usually based on measurements or records and represents the therapeutic decisions made by the orthopedic technician. The inner mold can be created variously in various ways. The inner mold/the molding represents all therapeutic decisions made and forms a kind of basis for the method described here.

Special procedures for producing the inner mold that should be pointed out here are digital methods for producing the inner mold. In the case of a digital method for creating the inner mold, the orthopedic technician creates a digital model (digital molding) of the measurement data and can incorporate their therapeutic decisions in this model. The inner mold is then present in the form of a digital model in a file. This file is subtractively or additively produced as an inner mold using a CNC machine. Production by additive FDM 3D printing [FDM=Fused Deposition Modeling] is preferred.

According to a combined manual/digital method for creating the inner mold, the orthopedic technician develops a conventional plaster cast molding, that is to say an inner mold of a plaster cast, which is then three-dimensionally scanned and subtractively or additively produced using a CNC machine. Production by additive FDM 3D printing is preferred.

According to a purely manual method for creating the inner mold, or the molding, the orthopedic technician develops a conventional plaster cast molding, which only later is scanned to create the outer mold. In the actual casting process, step c), the molding created manually by the orthopedic technician itself is used as inner mold.

After step a), in step b) an outer mold matching the inner mold is provided. The inner mold can be inserted into the outer mold in order to form the (complete) casting mold for producing the orthopedic support element. The outer mold can be created, for example, on the basis of the inner mold, in that an oversize, which predefines the later thickness of the orthopedic support element to be created by the method, is discharged onto the inner mold around the full periphery.

In the event of creating the outer mold on the basis of the three-dimensional/digital representation of the inner mold, the orthopedic support element is digitally modelled around the inner mold. The digital method allows the production of a precise overlapping portion on the basis of the inner mold, which overlapping portion cannot be produced by conventional, purely manual methods for creating orthopedic support elements. The orthopedic support element is thus precisely matched to the patient's body and can at the same time have an overlapping portion of this type.

As seen in a two-dimensional plan view, the orthopedic support element is modelled helically around the inner mold, with the result that a fillable cavity in the form of an open (helical) cylinder, the open ends of which are superposed/overlap, results between the outer mold and inner mold. This is done by suitably shaping the outer mold, in the course of which the outer mold comes to surround the overlapping portion at least in certain portions on both sides.

The casting mold has a mold portion, belonging to the outer mold, that rests against the inner mold and separates the open ends (first open end and second open end of the orthopedic support element) from one another for the casting operation. This mold portion provides a distance between the open ends.

When assembled, the outer mold and the inner mold enclose the fillable cavity.

It is important for the production of an orthopedic support element having the described overlapping region that the outer mold (or a mold portion of the casting mold that can be assigned to the outer mold) surrounds the overlapping region at least in certain portions on both sides. What is meant here is that, during the casting process, there is material of the outer mold (or material of a mold portion of the casting mold that can be assigned to the outer mold) on both sides of that region of the orthopedic support element that is part of the overlapping region. The orthopedic support element is usually sheet-like, with the result that the two sides of the orthopedic support element are clearly identifiable. The term "sheet-like" here means a sheet-like form when the orthopedic support element does not rest against the body part but has been taken off of, or to some extent "unwound" from, the body part. The material of the outer mold is then located on both sides. The outer mold does not need to be unipartite for this. It is even preferable for the outer mold to have multiple parts and for respective different parts of the outer mold to cover different sides of the orthopedic support element in the region of the overlapping portion.

The inner mold/the molding is usually digitalized by the production of the outer mold by a 3D scanning method at the latest. On the basis of these 3D data, a multi-part casting mold is generated with CAD software and produced using 3D printing technology.

In order to be able to align the inner mold and the outer mold with one another, an adjustment means is advantageous. The adjustment means results from mechanically connecting the mold parts to one another, e.g. by clamping the mold parts of the inner and the outer mold in one another, for example using plug-in or screwed connections. The adjustment means can be formed, for example, by studs on the inner mold and corresponding recesses, or cutouts, on the outer mold that engage in one another.

To scan the inner mold, it is advantageous if markers are provided on the inner mold that are also scanned, in order to facilitate exact alignment/positioning of the molding and outer mold in relation to one another later on.

Such additional markers make it easier to model and adjust the mold parts of the inner and the outer mold in relation to one another. Such additional markers are preferably fixedly connected to the inner mold and remain on the inner mold even during the casting process. These additional markers may be fastened at a suitable point on the inner mold, but preferably at the proximal end (facing the body) of the inner mold, at which end (in the case of conventionally produced moldings) a reinforcing rod is frequently also not enclosed by the plaster cast. Preferably, there is at least one such marker on the inner mold. Particularly preferably, there are enough markers, or one marker designed in such a way, that exact three-dimensional positioning and orientation of the inner mold is possible using the markers.

When the inner mold is produced using digital methods, the adjustment means and/or markers can also be provided directly on the inner mold by 3D printing methods. The same of course applies to the outer mold. Preferably, the additional structures (adjustment means and/or markers) are not inside the cavity that is filled in step c).

The concept of the use of adjustment means and markers to scan the molding in the correct alignment, or to correctly position the molding/inner mold and outer mold in relation to one another, can also be applied irrespective of the further method steps described here.

The particular feature of the casting mold provided by method steps a) and b) is that this casting mold predefines an overlapping portion, in that the outer mold (or a mold portion of the casting mold that can be assigned to the outer mold) surrounds the overlapping portion on both sides. The orthopedic support element has a sheet-like form and thus has two sides (also referred to as first side and second side or else as inner side and outer side below). In this context, the term "surround" means that the outer mold, in certain portions, predefines both the first side and the second side, or both the inner side and the outer side, of the orthopedic support element.

By joining the individual parts of the outer mold together, it is possible to provide a fillable space in the form of a helix in a two-dimensional plan view, thereby forming the open three-dimensional cylinder that can be filled in step c).

In step c), the orthopedic support element is created by filling an intermediate space between the inner mold and outer mold, or the casting mold, with a casting material. Until the casting takes place, throughout the process there is no positive mold of the orthopedic support element. Finding the mold for the product is done digitally. This constitutes a considerable advantage over known methods for creating orthopedic support elements of this type.

In step c), any desired casting method can be applied, in particular also injection molding, die casting or vacuum casting. Particularly preferable is a casting method which is carried out in a vacuum or at least a partial vacuum at an atmospheric pressure below 0.5 bar, because this makes it possible to avoid the formation of bubbles during the casting method particularly effectively.

The method is particularly advantageous when, in the region of the overlapping portion, the outer mold has a surface shape which corresponds to the surface shape of the inner mold at least in certain portions.

When the orthopedic support element is placed against the body part, in the overlapping portion there are preferably two zones of the orthopedic support element that lie one on top of the other. These zones lying one on top of the other preferably correspond to the first open end and the second open end of the orthopedic support element. In this respect, an inner surface of the orthopedic support element rests against the body part to be treated. Furthermore, in the overlapping portion, part of the inner surface of the orthopedic support element rests against an outer surface of the orthopedic support element. Preferably, that region of the inner surface that rests against the body part transitions smoothly into that region of the orthopedic support element that rests against the outer surface of the orthopedic support element. To that end, it is generally necessary for a surface of the outer mold to correspond at least in certain portions (regions) to the surface of the inner mold, because a gentle, smooth transition between that region of the inner surface that rests against the outer surface of the orthopedic support element in the overlapping portion and that region of the inner surface that rests against the body part is enabled in this way. The area in which the surface shapes of the inner mold and outer mold correspond can be a surface area or else a linear region.

The method is furthermore advantageous when the outer mold forms a transitional region to the overlapping portion, in which transitional region the outer mold rests against the inner mold in a sheet-like manner.

In this region, the shape of the inner surface of the orthopedic support element that was produced by the casting method also does not exactly correspond to the shape of the inner mold, or of the molding; rather, here there is a distance between the inner mold, or the form of the molding, and the inner surface, which is predefined by the mold portion of the casting mold that predefines the overlapping portion.

This distance also requires that the orthopedic support element be (slightly) curved in relation to a shape predefined by a casting mold when it is placed against the body part to be treated. However, this curvature is small enough that the therapeutic action of the orthopedic support element is not adversely affected thereby. The distance created by the mold portion, or by the casting mold, is preferably less than 10 mm [millimeters], particularly preferably less than 5 mm, but usually more than 0.5 mm, preferably more than 1 mm, in order that a sufficiently stable separation of the open ends of the orthopedic support element during the casting operation or during any other desired method for producing the orthopedic support element is achieved. This distance can be compensated by very slightly curving the orthopedic support element when the orthopedic support element is being placed against a body part to be treated, this having no effect on the therapeutic action of the orthopedic support element. The form in which the orthopedic support element is produced and in which the distance is provided between the two open ends of the orthopedic support element is referred to here as production molding. The form in which the orthopedic support element is placed against the body part to be treated and is (slightly) curved in relation to the production molding is referred to as therapy shaping.

A sheet-like bearing surface is thus formed between the outer mold and the inner mold in the overlapping region. At this sheet-like bearing surface, there is contact that is sealed in relation to the casting material between the inner mold and the outer mold, which leads to the casting material that later forms the orthopedic support no longer resting against the inner mold in this region, but being surrounded on both sides by the outer mold. The formation of the overlapping region is made possible in that the outer mold surrounds the orthopedic support element in certain portions on both sides.

The method is furthermore advantageous when the outer mold has multiple parts, and a first part of the outer mold predefines a first side of the overlapping portion while a second part of the outer mold predefines a second side, opposite the first side, of the overlapping portion.

The outer mold preferably consists of at least two or more parts. In order to be able to detach the cast orthopedic support element from the casting mold later on, a subdivision of the outer mold is advantageous. As an alternative, a unipartite outer mold or even a unipartite casting mold, in the case of which the inner mold and outer mold are printed out together by a 3D printer, can also be produced within the scope of method steps a) and b). In that case, steps a) and b) are integrated with one another. In such embodiment variants, however, it is then usually necessary to destroy the casting mold (inner mold and/or outer mold) in order to detach the finished orthopedic support element from the casting mold. This can be done, for example, by chemical dissolution of the casting mold or by burning off the casting mold.

It is even particularly preferable if the outer mold has three parts. In that case, a first part and a second part surround the overlapping portion on both sides, as described. Furthermore, there is a third part which forms a part of the outer mold opposite the overlapping portion. The term "opposite" here denotes in particular a region of an opposite side of the inner mold.

The method is also advantageous if at least the outer mold is also produced by a three-dimensional printing method.

This in particular includes additive printing methods. As an alternative, however, it is also possible to use three-dimensional subtractive methods, such as for example CNC milling, to produce the outer mold.

During the production of the outer mold, various structures can also be created which later serve to carry out the casting in step c) without problems. For example, runners, feeders and risers can be provided.

Three-dimensional printing methods enable the production of objects from various materials based on digital three-dimensional models. In this respect, the digital model is additively built up in layers by computer-controlled machine tools. There are various methods that are grouped together under the expression 3D printing. For example: selective laser sintering (SLS), fused deposition modeling (FDM). All possible ways of forming digital 3D models by additive methods can be used for producing the orthopedic support element.

The use of a three-dimensional printing method facilitates efficient production of such a complex outer mold as is required for the formation of the described overlapping portion.

The method is also advantageous if the casting material is a silicone material.

Silicones are particularly compatible with the body. Firstly, the material is non-toxic to humans and animals; secondly, the material is comfortable to wear on the skin. The therapeutic advantage of soft material such as silicone is that an orthosis manufactured therefrom supports the existing functionality of the body. By contrast with hard materials, movements are possible and the body part to be treated does not stiffen in the course of therapy.

According to further configurations, the method can also be used to produce elements on the orthopedic support element with higher elaborateness than the elaborateness that can be achieved by the 3D printing method for producing the outer mold. To that end, prefabricated objects (for example logos or the like) can be integrated into the outer mold. The high processing accuracy of silicone as casting material, however, already allows very fine resolutions. Functional elements of other materials, for example closures, reinforcements or adapters to other orthopedic devices, can be integrated, adjusted in terms of shape, and integrally molded in geometries generated by software. It is also possible to integrate functional structures of various materials in the outer mold or the inner mold using a 3D printer, the functional structures being integrally molded during the casting in step c). After the casting, the elements are detached from the mold and remain in the orthosis. 3D printers can print various materials with various properties and, depending on the 3D printing method, also modify the properties of a material in a printing process. In order for this to be possible, the mold and functional parts should be produced in a printing process or the various parts should be preproduced and later assembled. Special 3D printing materials that can be detached with a liquid solvent enable cavities inside the orthosis by virtue of detachable cores.

Moreover, functional geometries of the orthopedic support element, such as for example closures, a partially overlapping and tapering edge, stiffening as a result of greater material thicknesses, elasticity enhancing elements, and weight reduction means, such as porous bodies and/or ventilation structures, can be integrated in the outer mold and the inner mold. In particular, identifiers can be made by cutouts modeled in the outer mold. These include, for example, patient data, production date and information about the orthopedic manufacturer's workshop. Furthermore, individual, personal esthetic designs can be incorporated in the orthopedic support element.

In step c), multiple-stage casting methods can also be applied. In multiple-stage casting methods, elements of other materials and/or of silicone with different degrees of hardness can be processed and integrated. This makes it possible to provide different hardnesses of the orthopedic support element. By dissolving out closed cavities that are filled in further processes, it is possible to provide various casting materials selectively at certain positions within the orthopedic support element. To that end, a mold is preferably produced from a non-soluble material which is supplemented by sub-molds or cores of soluble materials. In that case, first of all the silicone is cast into the cavity of the mold. After wetting, the sub-molds or cores are dissolved away step by step. The newly created cavities of the dried mold are filled.

After the casting process (step c)) has finished, the orthopedic support element is firstly detached from the casting mold (formed of the inner mold and outer mold). To that end, release agents can be used. Suitable release agents are, for example, Teflon spray or wax. If appropriate, the detachment from the casting mold can also be done with compressed-air assistance.

The method described makes it possible to produce orthopedic support elements which from a technical perspective have a higher quality than orthopedic support elements produced by the known rolling method. For example, gas accumulations at functional geometries (for example close to reinforcements of the orthopedic support element) can be effectively avoided. Furthermore, a clear, precise shape of the entire orthopedic support element can be ensured.

Furthermore, certain particularly complex geometries cannot be produced by the conventional methods, or can be produced by them only over a long period of time. Such particularly complex geometries can be produced precisely by the method described. Moreover, the range of therapeutic application of such orthopedic support elements is expanded. By contrast to the conventional production technology, which only makes hand and foot orthoses possible, the method described here makes it possible to produce orthopedic support elements for all regions of the body in all sizes from silicone. This also applies, for example, to orthopedic support elements for the entire torso of a human being.

In a further preferred embodiment, the orthopedic support element in the manufacturing shaping is produced by a printing method. The orthopedic support element is thus printed directly. The printing method is a 3D printing method. It is possible to print silicone directly with suitable 3D printing methods. As a result of the distance that is predefined in the production shaping of the orthopedic support element, it becomes possible to print the first open end and the second open end of the orthopedic support element without creating a material bond between the first open end and the second open end. During the printing method, it is possible to also print support structures for supporting the wholly or partially printed support element that are removed again later (after the printing method has finished). All the details described further above relating to printing methods for producing a casting mold can also be transferred to the printing method for directly printing the orthopedic support element.

Also to be described here is an orthopedic support element for correcting an orthopedic abnormality of a body part, which orthopedic support element can be placed against the body part to be corrected, having an overlapping portion, in which the orthopedic support element overlaps itself when it is placed against the body part to be corrected.

This orthopedic support element is (as described further above) produced by a casting method or a printing method.

This orthopedic support element is particularly preferably produced by the method described.

The particular advantages and design features explained for the method described can be applied and transferred analogously to the orthopedic support element. The same applies to the particular advantages and design features described below of the orthopedic support element, which can be applied and transferred to the method in any desired way.

Preferably, the orthopedic support element is slightly curved in relation to a manufacturing shaping (that it had during the production) and is brought into a therapy shaping when it is placed against the body part to be corrected.

The production shaping and the therapy shaping differ in that there is a distance between the two open ends of the orthopedic support element in the manufacturing shaping and these two open ends rest against one another in the therapy shaping. In the production shaping, the material of the orthopedic support element is preferably completely relieved of tension. In the therapy shaping, there is a (very slight) curvature by which the orthopedic support element is curved such that the two open ends rest against one another (in the overlapping portion). The distance between the two open ends in the production shaping is preferably less than 10 mm [millimeters], particularly preferably less than 5 mm, but usually more than 0.5 mm, or even more than 1 mm, in order that a sufficiently stable separation of the open ends of the orthopedic support element during the casting operation is achieved.

The orthopedic support element further preferably consists of silicone.

It is also preferred when the orthopedic support element has at least one of the following structural features that were also produced by the casting method for producing the orthopedic support element:

at least one closure means,
at least one inlay,
at least one decoration, or
at least one identifier.

Such structural features may in particular also be created in that prefabricated objects are also integrated in the casting mold, which then at least partially form the structural features cited. As an alternative or in addition, such structural features can also be manufactured from the material of the orthopedic support element during the casting process. All details disclosed further above within the context of the described method can contribute to the formation of (additional) structural features on the orthopedic support element.

Figure 2:
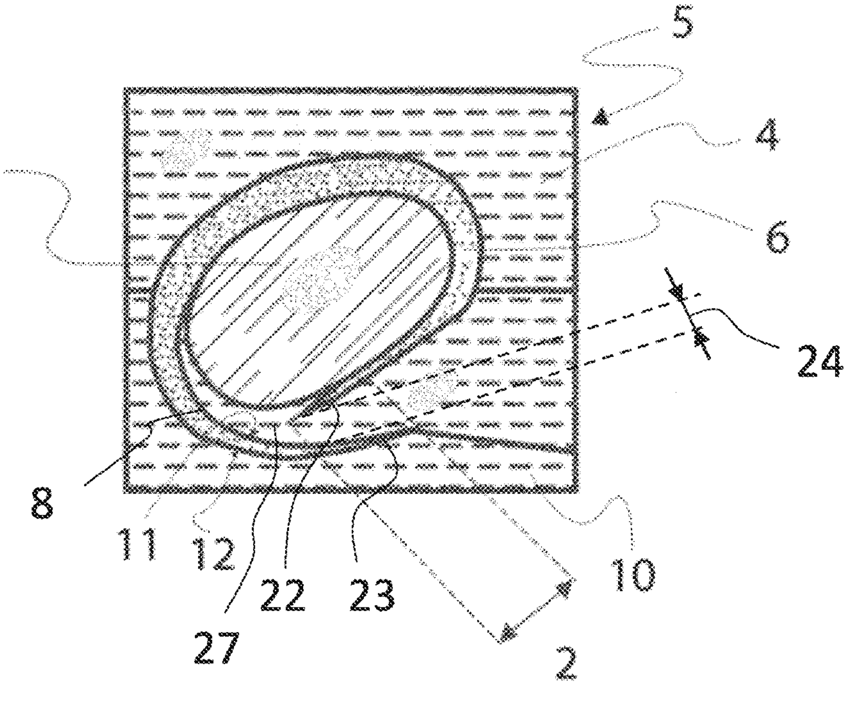
Figure 3:
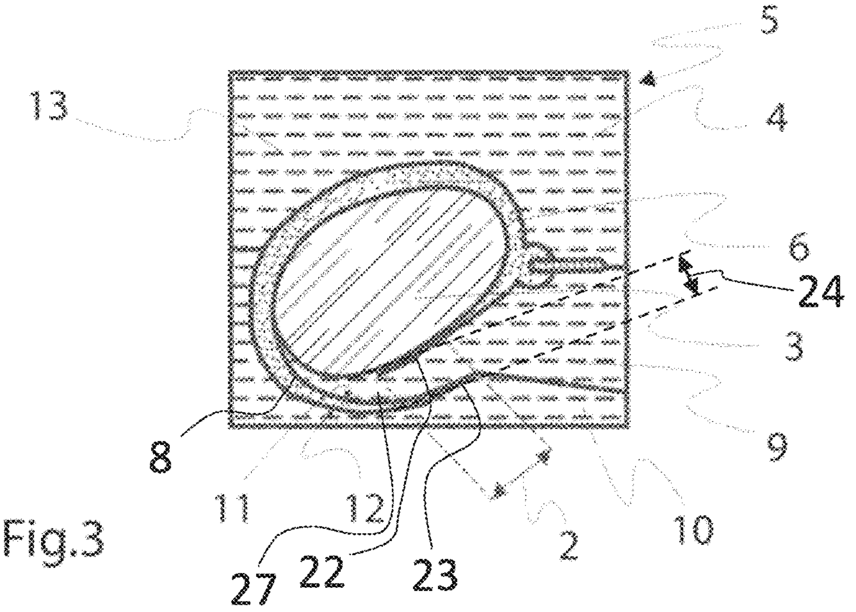
Figure 4:
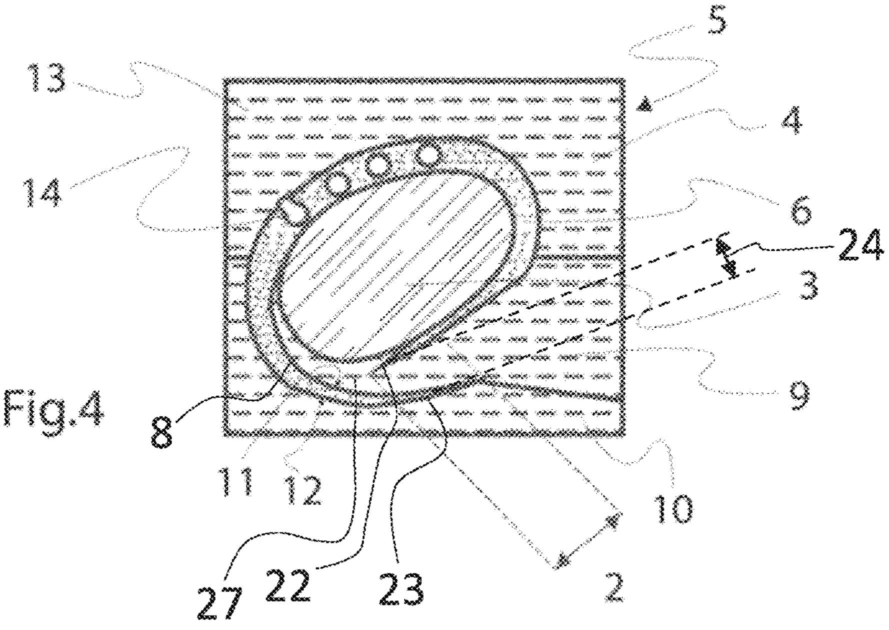
Figure 5:
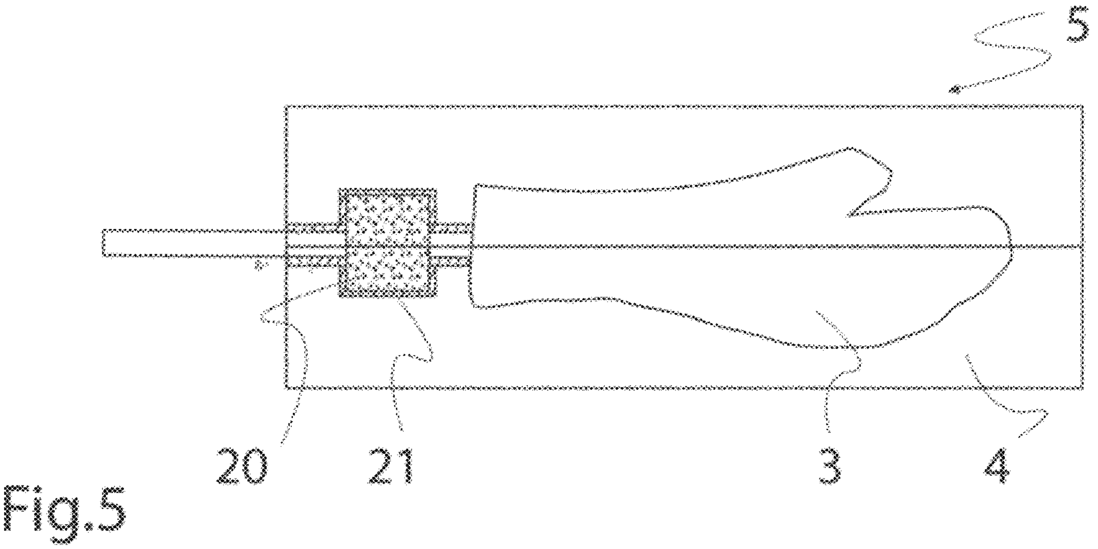
Figure 6:
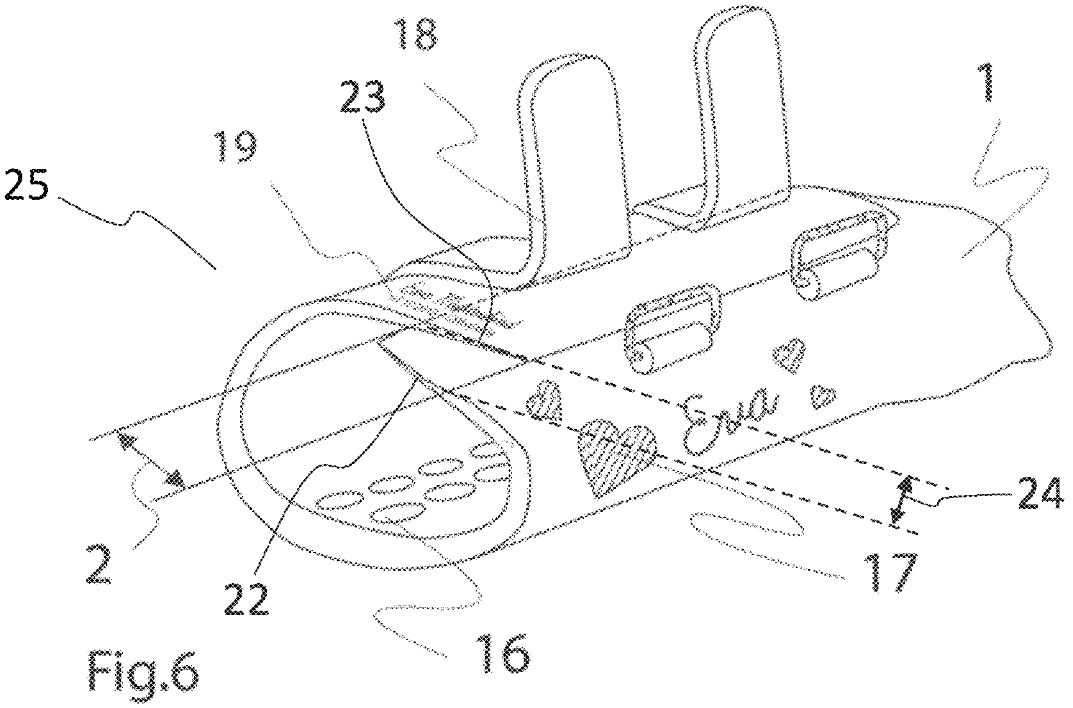
Figure 7:
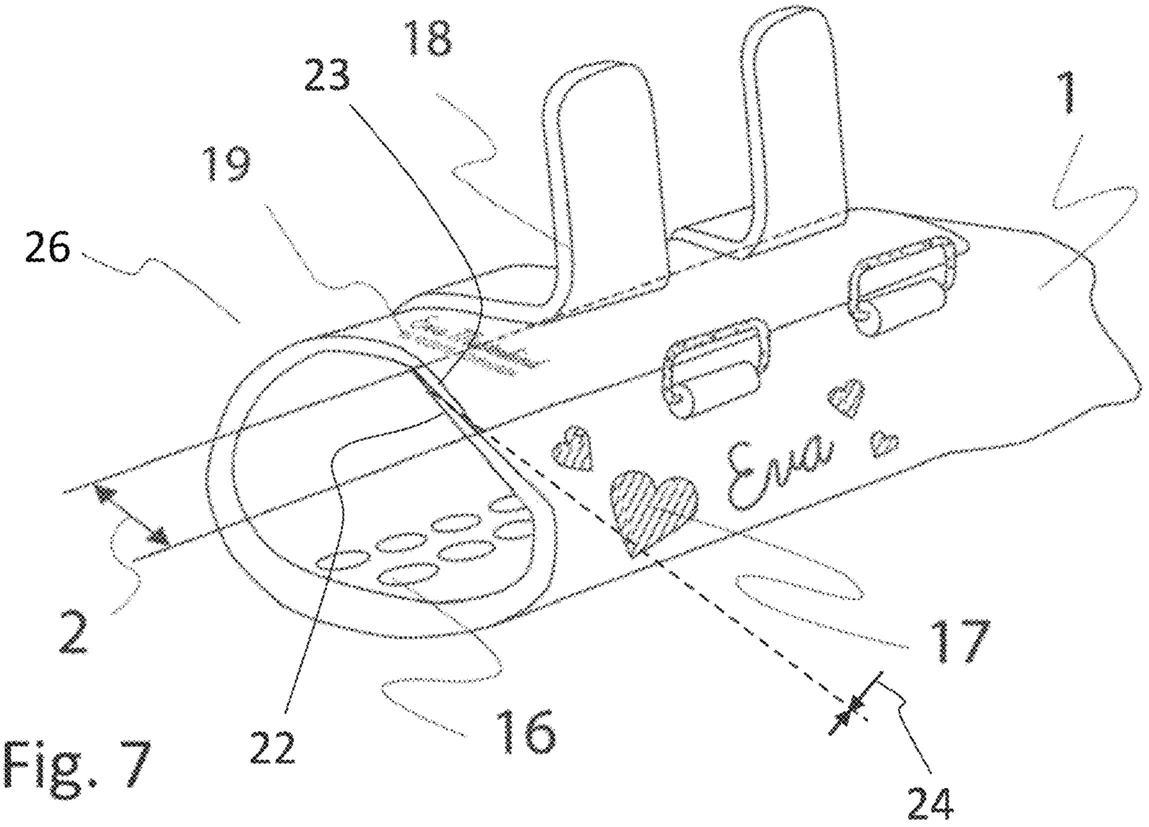

The invention and the technical field are explained in more detail below on the basis of the figures. The figures depict particular embodiment variants, although the invention is not restricted to them. In particular, it should be noted that the figures and the relative sizes illustrated therein are only schematic. In the figures:

FIG. 1: shows a first sectional view through a casting mold for producing an orthopedic support element, FIG. 2: shows a second sectional view through a casting mold for producing an orthopedic support element, FIG. 3: shows a sectional view through a further casting mold for producing an orthopedic support element, FIG. 4: shows a sectional view through yet another casting mold for producing an orthopedic support element, FIG. 5: shows a sectional view through a further casting mold for producing an orthopedic support element, FIG. 6: shows an orthopedic support element in the production shaping, and FIG. 7: shows the orthopedic support element from FIG. 6 in the therapy shaping.

FIG. 1 shows a sectional view through a casting mold 5 for the production of a described orthopedic support element, this casting mold being formed from an inner mold 3 and outer mold 4. In this case, the outer mold also has runners 15, which assist the casting process for producing the orthopedic support element. Illustrated in the casting mold 5 according to FIG. 1 is the casting material 6, from which the orthopedic support element is produced. Through these runners 15, for the one part the casting material 6 for producing the orthopedic support element can enter the casting mold 5. For the other part, through such channels gas can leave the casting mold 5 when the casting material 6 enters the casting mold 5.

FIGS. 2, 3 and 4 show a schematic cross section of casting molds 5 according to FIG. 1. Also illustrated here is the overlapping portion 2. The overlapping portion 2 is formed by a mold portion 27 predefined by the outer mold 4. Adjoining the overlapping portion 2 is the transitional region 8, in which a transition from the inner mold 3 to the outer mold 4 is formed. In the transitional region 8, the mold portion 27 rests against the inner mold 3. The mold portion 27 predefines a first open end 22 and a second open end 23 of the orthopedic support element, or of the casting mold 5, at a distance 24 from one another. The casting mold illustrated in FIG. 2 has three parts, with an inner mold 3 and an outer mold 4 which in turn consists of a first part 9 and a second part 10. The casting mold 5 predefines a first (inner) side 11 and a second (outer) side 12 of the orthopedic support element. These two sides are opposite one another in the region of the overlapping portion 2. The mold portion 27 is between these two sides.

FIG. 3 and FIG. 4 show sectional views through two further, different casting molds for the described method. Also visible here in each case are the inner mold 3 and the outer mold 4. Each outer mold here consists of multiple parts, specifically a first part 9, a second part 10 and a third part 13. The outer mold 4 and the inner mold 3 together form a cylindrical (helical) hollow region, which is filled with the casting material 6 in order to produce the orthopedic support element. An overlapping portion 2 of the orthopedic support element is formed by the outer mold 4. The orthopedic support element overlaps itself in this overlapping portion. A first part 9 of the outer mold 4 in this case determines the shape of a first side 11 of the overlapping region 2. A second part 10 of the outer mold 4 determines the shape of a second side 12 of the overlapping region 2. The third part 13 is arranged on that side of the inner mold 3 that is opposite the first part 9 and the second part 10. The first part 9 and the second part 10 together form a half shell of the casting mold 5, while the third part 13 forms the other side of the casting mold 5.

FIG. 4 shows, as a special feature and by way of example, that inlays 14 are inserted in the casting mold 5, which are encased by the casting material 6 during the casting process in step c).

FIG. 5 shows an adjustment means with the inner mold 3 and outer mold 4 being arrested relative to one another. Shown here, for example, is a recess 21 in the outer mold 4 and a stud 20 on the inner mold 3.

FIG. 6 shows a finished orthopedic support element 1, which was produced according to the described method, in a manufacturing shaping 25, which in particular corresponds to the form predefined by the casting mold. As a result of the production method, ventilation means 16, decorations 16, closure elements 18 or other fixtures, and individualizations and identifiers 19 can be provided on the orthopedic support element without problems. In FIG. 6 it is possible to see, in three dimensions, the overlapping portion 2 in which a first open end 22 and a second open end 23 of the orthopedic support element 1 overlap. In the manufacturing shaping, there is a distance 24 between the first open end 22 and the second open end 23.

FIG. 7 shows the orthopedic support element 1 according to FIG. 6 in a therapy shaping 26, although the body part to be treated is not illustrated here. The therapy shaping 26 and the manufacturing shaping 25 differ in that the first open end 22 and the second open end 23 rest against one another, and accordingly without a distance 24 between them, in the therapy shaping 26.

LIST OF REFERENCE SIGNS

1. Orthopedic support element
2. Overlapping portion
3. Inner mold
4. Outer mold
5. Casting mold
6. Casting material
7. Surface shape
8. Transitional region
9. First part
10. Second part
11. First side
12. Second side
13. Third part
14. Inlay
15. Runner
16. Ventilation means
17. Decoration
18. Closure element
19. Individualization
20. Stud
21. Recess
22. First open end
23. Second open end
24. Distance
25. Manufacturing shaping
26. Therapy shaping
27. Mold portion

The invention claimed is:

1. A method for producing an orthopedic support element having an overlapping portion, in which the orthopedic support element overlaps itself when it is placed against a body part to be corrected, wherein, for production, a manufacturing shaping of the orthopedic support element is predefined, in which the manufacturing shaping differs from a therapy shaping of the orthopedic support element when being placed against the body part to be corrected, wherein there is a distance between a first open end and a second open end of the orthopedic support element in the overlapping portion of the manufacturing shaping that is not present in the therapy shaping, wherein the method comprises a casting method and wherein the distance between the first open end and the second open end of the orthopedic support element in the manufacturing shaping is predefined by a mold portion of a casting mold, and wherein the method comprises:

producing an inner mold by a representation of the body part, the inner mold predefining a posture of the body part, providing an outer mold, wherein the outer mold together with the inner mold forms the casting mold for producing the orthopedic support element from a casting material, and casting the orthopedic support element using the casting mold, formed from the outer mold and inner mold, and the casting material, wherein the outer mold surrounds the overlapping portion at least in certain portions on both sides.

2. The method as claimed in claim 1, wherein, in a region of the overlapping portion, the outer mold of the casting mold has a surface shape which corresponds to the surface shape of the inner mold at least in certain areas.

3. The method as claimed in claim 1, wherein the outer mold of the casting mold forms a transitional region to the overlapping portion, in which the transitional region of the outer mold rests against the inner mold in a sheet-like manner.

4. The method as claimed in claim 1, wherein the outer mold of the casting mold has multiple parts, and a first part of the outer mold predefines a first side of the overlapping portion while a second part of the outer mold predefines a second side, opposite the first side, of the overlapping portion.

5. The method as claimed in claim 1, wherein at least the outer mold of the casting mold is produced by a three-dimensional printing method.

6. The method as claimed in claim 1, wherein at least the inner mold of the casting mold is produced by a three-dimensional printing method.

7. The method as claimed in claim 1, wherein the orthopedic support element is casted from a silicone material.

* * * * *